(12) United States Patent
Phan et al.

(10) Patent No.: US 6,665,065 B1
(45) Date of Patent: Dec. 16, 2003

(54) DEFECT DETECTION IN PELLICIZED RETICLES VIA EXPOSURE AT SHORT WAVELENGTHS

(75) Inventors: Khoi A. Phan, San Jose, CA (US); Bhanwar Singh, Morgan Hill, CA (US); Wolfram Porsche, Dresden (DE)

(73) Assignee: Advanced Micro Devices, Inc., Sunnyvale, CA (US)

( * ) Notice: Subject to any disclaimer, the term of this patent is extended or adjusted under 35 U.S.C. 154(b) by 75 days.

(21) Appl. No.: 09/829,195

(22) Filed: Apr. 9, 2001

(51) Int. Cl.[7] .............................................. G01N 21/00
(52) U.S. Cl. .................................. 356/237.1; 356/237.5
(58) Field of Search ......................... 356/237.1–237.6, 356/445–448, 394, 398; 250/571–522; 378/161, 34; 430/30, 311, 330; 34/61; 382/144–149

(56) References Cited

U.S. PATENT DOCUMENTS

| | | | |
|---|---|---|---|
| 4,716,299 A | * 12/1987 | Tanaka et al. | 250/571 |
| 5,796,484 A | * 8/1998 | Honma et al. | 356/237.1 |
| 5,900,354 A | * 5/1999 | Batchelder | 430/395 |
| 5,940,175 A | * 8/1999 | Sun | 356/237.3 |
| 5,989,763 A | * 11/1999 | Bendik et al. | 430/30 |
| 6,097,790 A | * 8/2000 | Hasegawa et al. | 378/161 |
| 6,279,249 B1 | * 8/2001 | Dao et al. | 34/61 |
| 6,327,021 B1 | * 12/2001 | Higashiguchi | 355/30 |
| 6,363,166 B1 | * 3/2002 | Wihl et al. | 356/398 |

OTHER PUBLICATIONS

Brian J. Grenon, et al. "Formation and Detection of Sub–Pellicle Defects by Exposure to DUV System Illumination". SPIE vol. 3873, pp. 162–176. Sep. 1999.

* cited by examiner

*Primary Examiner*—Frank G. Font
*Assistant Examiner*—Sang H. Nguyen
(74) *Attorney, Agent, or Firm*—Amin & Turocy, LLP

(57) ABSTRACT

A system and method are provided for detecting latent defects in a mask or reticle, which defects may vary as a function of radiation at exposure wavelengths. By way of example, the mask or reticle is inspected, exposed to radiation at a specified wavelength, and then reinspected. A correlation between the inspection results before and after exposure provides an indication of exposure-related defects, which may include defect growth and/or formation of defects caused by the exposure. By way of further illustration, the combination of inspection and exposure of a mask or reticle may be implemented with respect to a pellicized mask or reticle so as to detect additional defects related to use of the pellicle with the mask or reticle.

36 Claims, 10 Drawing Sheets

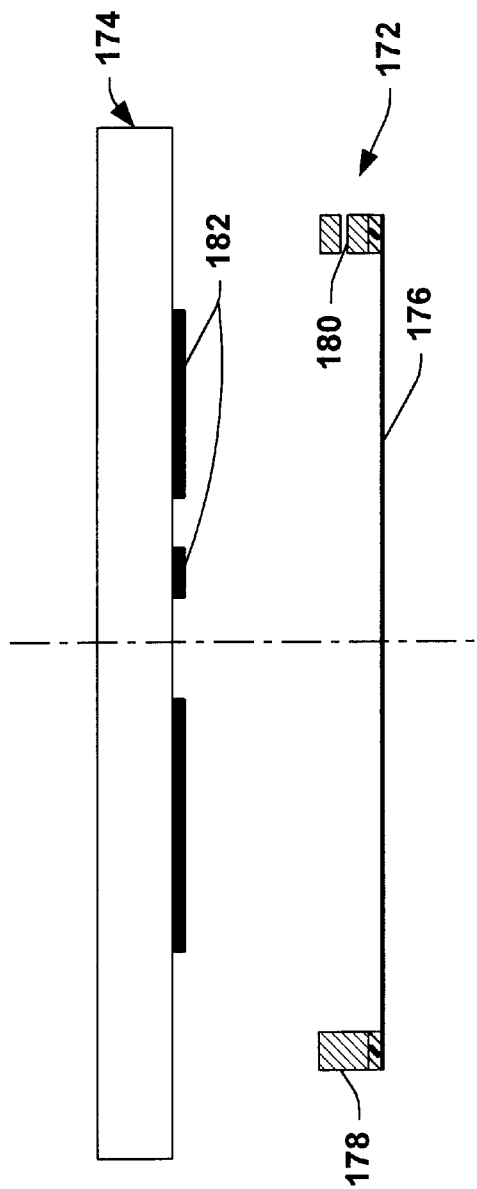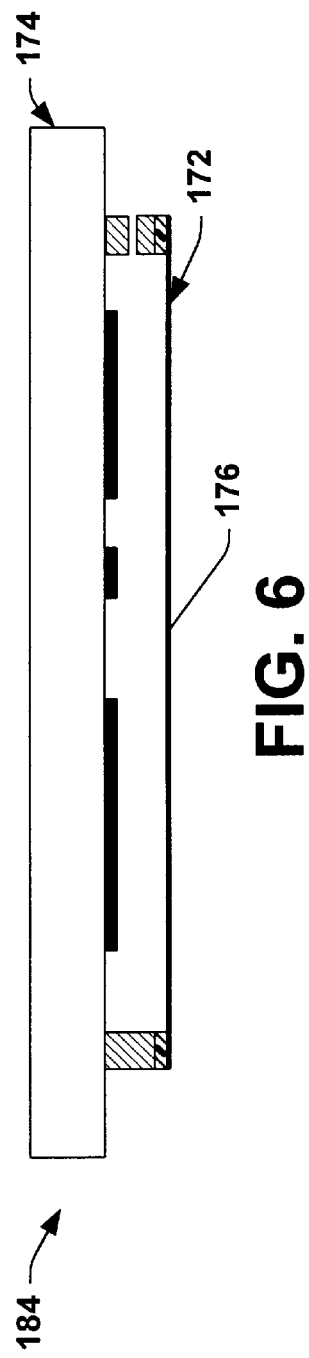

DEFECT DETECTION IN PELLICIZED RETICLES VIA EXPOSURE AT SHORT WAVELENGTHS

FIELD OF THE INVENTION

The present invention generally relates to semiconductor processing and, more particularly, a system and method to detect defects in a pellicized reticle due to exposure at short wavelengths.

BACKGROUND OF THE INVENTION

Lithography in semiconductor processing relates generally to the process of transferring patterns which correspond to desired circuit components onto one or more thin films that overlie a substrate. Patterns are transferred from a photomask or reticle onto a photoresist layer which overlies the film on the wafer through an exposure process. If the photomask or reticle contains defects, even submicron in range, such defects may be transferred to a wafer during the exposure. Such defects may be generated by the fabrication process utilized to produce the mask or reticle as well as during subsequent handling and processing. Such defects generally fall into two classes: fatal (or killer) defects and nonfatal defects.

Defects may arise at any stage of semiconductor fabrication, such as during manufacture of a blank reticle or mask or the process steps employed to manufacture a desired reticle.

Inspection tools have been developed and proposed to detect defects in the mask or reticle, such as upon completion of the mask or reticle fabrication sequence. A typical inspection process may examine several characteristics of the mask or reticle, such as linewidth measurements, measurement of the registration among die patterns, determining that all intended features have been transferred to the mask or reticle, and determining if any mask fabrication defects have been produced. Different tools may be utilized for each of these inspections.

By way of particular example, mask fabrication defects are usually located by using transmitted light. The inspection task determines if there is light or no light transmitted at a particular location on a reticle as a function of the intended design. The determination may involve both die-to-die inspections, which involve a visual comparison of two equivalent pattern areas in an array of a die. Any differences are attributable to defects in one or the other inspected regions. A die-to-die inspection, however, cannot detect defects that affect the entire die equally. Accordingly, another type of inspection, called die-to-database inspection, may be utilized. Die-to-database inspection compares an optical image with a simulated image derived from the original design data. This approach, however, requires considerably more image processing power.

After a reticle or mask is determined to sufficiently free from defects a pellicle may be attached to provide protection. The pellicle attachment and/or features of the pellicle itself (e.g., frame films, ventilation, adhesives, etc.), however, may contaminate the reticle as well as generate defects. A pellicle is a membrane that seals off the mask or reticle surface from airborne particulates and other forms of contamination. The membrane is mounted on a metal frame that is attached to the chrome side of the mask or reticle, such that the membrane is suspended above the mask surface. A pellicle also may be mounted to the other surface. While pellicle helps protect the reticle or mask from subsequent contamination, the pellicle and the process of attaching the pellicle provides another place where defects can arise. Accordingly, post-pellicle inspection usually is employed to ensure that no additional defects are caused by the pellicle.

Post-pellicle inspection may be implemented by mounted the mask-pellicle assembly in a projection aligner. Then, the projection aligner is employed to expose round, thin glass wafers that are coated with chrome and resist. The wafers are exposed, developed and etched and stripped to produce an image suitable for inspection by transmitted light. The processed wafers may then be processed on an automatic mask inspection system, such as described above. Defects located on the inspection system that coincide in location on two or more glass wafers are attributable to defects resulting from the application of the pellicle.

Defects further may develop during post-pellicle fabrication, which may include electrostatic discharge (ESD), as well as circumstances associated with reticle storage, the fabrication environment and stepper usage.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

A system and method are provided for detecting latent defects in a mask or reticle, such as to detect defects that may vary as a function of radiation at exposure wavelengths. One aspect of the present invention provides an inspection system utilized in combination with an exposure system. The inspection system is utilized to detect defects in the mask or reticle and store associated inspection data. The exposure system illuminates the mask or reticle with an exposure wavelength, such as to simulate actual exposure experience by the mask or reticle during semiconductor fabrication. Inspection data may be collected for both during and after exposure. A correlation between the inspection data provides an indication of exposure-related defects, which may include defect growth and/or formation of defects caused by the exposure.

According to another aspect of the present invention, the combination of inspection and exposure of a mask or reticle may be implemented with respect to a pellicized mask or reticle. As a result, additional defects, such as transmission degradation, related to use of the pellicle with the mask or reticle under exposure may be detected.

Another aspect of the present invention provides a method of detecting defects in a mask or reticle. The method includes inspecting a mask or reticle and then exposing the mask or reticle to an exposure wavelength. A post-exposure inspection is performed and the inspection information for both before and after exposure is correlated. The correlation provides an indication of defects functionally related to the exposure. As a result of identifying such defects, the occurrence of exposure-related defects during fabrication may be mitigated.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

BRIEF DESCRIPTION OF THE DRAWINGS

FIG. 5 is an exploded side elevation illustrating a pellicle being attached to a mask or reticle;

FIG. 6 is view of a pellicized reticle;

DETAILED DESCRIPTION OF THE INVENTION

The present invention provides a system and method that facilitates early detection of defects in a mask or reticle, such as may be generated due to exposure of a patterned reticle. The present invention further provides a system and method operable to detect transmission degradation at exposure wavelengths. One aspect of the present invention provides such defect detection by inspecting surface characteristics of a mask or reticle after exposing the mask or reticle to radiation at exposure wavelengths (e.g., short wavelength radiation in the DUV range).

Figure 1:
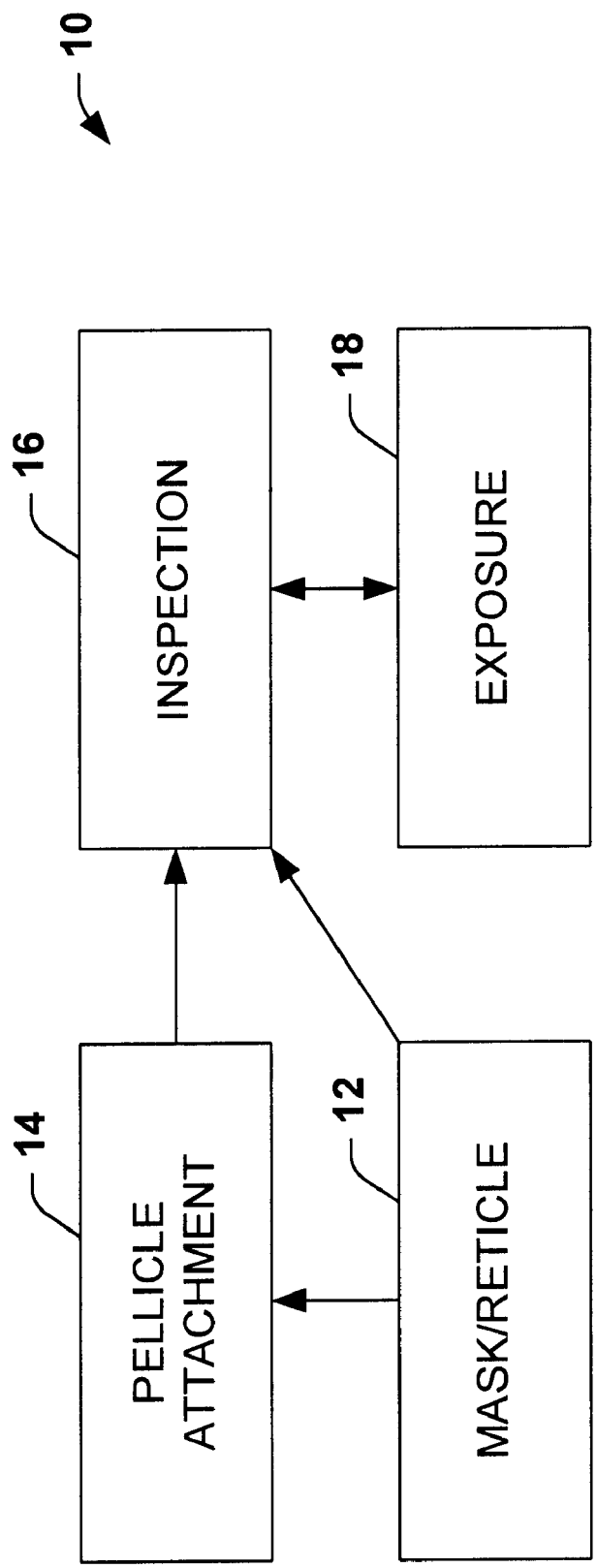
FIG. 1 is a schematic block diagram of a system that may be employed to detect defects in accordance with the present invention.

FIG. 1 illustrates a simplified functional block diagram of a system 10 operative to detect defects associated with a mask or reticle 12 in accordance with an aspect of the present invention. In this example, it is assumed that a satisfactory patterned reticle has been produced, such as based on a confirming inspection. That is, the reticle may contain defects, but such defects are considered nonfatal defects, such as permit adequate pattern transfer onto a wafer.

A pellicle may be attached to the mask or reticle 12 through a pellicle attachment procedure 14 to provide a pellicized reticle or mask. As is known in the art, a Pellicle is a thin, transparent membrane that seals off the mask or reticle surface from airborne particulates and other forms of contamination. The membrane is mounted on a metal (e.g., Aluminum) frame that is securely fastened onto the reticle, such as by adhesive compounds. The pellicle typically is attached only onto the chrome side of the reticle or mask 12 for projection aligners. For steppers, the pellicles are usually bonded onto both the chrome and the glass sides of the reticle 12. Particles residing on the pellicle surface are located at a sufficient distance from the reticle surface so as to have a negligible effect on the wafer image.

The system 10 includes an inspection system 16 to detect defects in the mask or reticle 12. Such inspection may be performed on the mask or reticle 12 with and/or without a pellicle. In one aspect, the inspection system 16 includes both pattern inspection to located hard pattern defects as well as particulate inspection to expose soft contaminant based defects. By way of example, the inspection system 16 may employ transmitted light, reflected light, and/or scanned laser technologies. The inspection system 16 stores the inspection data in associated memory. The inspection data, for example, may include information characterizing each defect, including an indication of the defect location, its size, and severity. In one aspect, the inspection system 16 may include a die-to-die inspection in which two equivalent pattern areas are compared, with noted differences being attributed to defects in one of the inspected regions. In addition, die-to-database inspection may be employed by comparing an inspected region of the reticle 12 to a simulated image constructed based on the design data for the reticle.

By way of further illustration, the inspection system may be selected from the STARlight family of inspection tools, which are available from KLA-Tencor of San Jose, Calif. The inspection system, thus, is operative to inspect the mask or reticle 12 for contamination, such as particulate matter, transmission errors and electrostatic discharge (ESD) damage. It further may inspect one or more reticle surfaces, including the pellicle (when a pellicle is applied) and backside of the reticle 12.

After inspection by the inspection system 16, the mask or reticle 12 is placed in an exposure system 18 in which it is radiated by light having an exposure wavelength. In one aspect, the exposure chamber 18 applies radiation of a selected short wavelength to reticle or mask 12 to simulate wavelength exposure during an actual lithography process. By way of example, the exposure chamber may apply DUV radiation having a specified short wavelength, such as less than about 300 nm (e.g., 157 nm, 193 nm, or 248 nm). The exposure chamber further may apply the DUV radiation over an extended period of time, such as about to simulate about ten hours of usage over about a three month time period (e.g., about 900 to 1000 hours of exposure). The specified wavelength of light further may be applied as numerous pulses (e.g., about 5000 to about 10000 pulses) to further simulate exposure during actual fabrication. The exposure operates as an aging test, which may be applied to the mask or reticle 12 with or without the pellicle.

In addition, the exposure system 18 may include a source of an inert gas, such as nitrogen or helium. The inert gas provides an environment that facilitates radiation of the mask or reticle for shorter wavelength radiation, such as 157 nm. In an ambient environment, O2 and H2O tend to attenuate shorter wavelength radiation between a source of illumination and the mask or reticle 12. The inert gas environment further simulates conditions within a stepper or scanner in which electrostatic discharge (ESD) tends to occur. ESD may develop in such an environment and cause damage to the mask or reticle. Accordingly, the inert gas provides a means of quantifying the effects of ESD in an actual stepper and/or scanner environment.

After the exposure is completed, the mask or reticle 12 (with or without the pellicle) is inspected again by the inspection system 16. For example, when the inspection is performed without a pellicle, the sources of defects that are associated with the pellicle and its attachment to the mask or reticle are removed as variables. Consequently, the inspection system 16 may focus on the interaction between the exposure cycle by the exposure system 18 and the surface condition of the mask or reticle 12. That is, particulates, contaminants, and/or chemical moisture remaining on the surface of the reticle from the cleaning process can be quantified for defect growth and/or defect formation caused by exposure.

As mentioned above, the exposure and post-exposure inspection may be implemented with respect to a mask or reticle 12 having an associated pellicle. By way of example, after passing the pre-pellicle inspection, a pellicle may be attached to the good mask or reticle 12 and an additional aging test may be performed on the pellicized reticle in the exposure system 18. That is, the exposure system 18 exposes the pellicized reticle to short wavelength radiation, such as may include numerous pulses of light having a specified wavelength for an extended period of time. The post-exposure pellicized mask or reticle is then inspected.

The post-exposure inspection data is compared with the pre-exposure inspection data to discern whether new defects have formed and/or whether existing defects have grown. A comparison between such data helps quantify the long term effects of wavelength exposure, such as may affect pellicle transmission. An increase in the number defects and/or an increase in size, for example, may correspond to subpellicle defects that increase as a function of increasing wavelength exposure.

A mask or reticle failing the post-exposure inspection, may be recleaned, inspected, and radiated at exposure wavelength. Assuming the mask or reticle passes subsequent inspection, it may be repellicized. The pellicized mask or reticle is again inspected. The mask or reticle may then be exposed in the exposure chamber 18 and then inspected again to determine the existence of any defects that may be caused due to wavelength exposure. If the mask or reticle passes the additional post-exposure inspection, it may be shipped to the customer. In contrast, if the mask or reticle fails the additional post-exposure inspection, the current cleaning and/or pellicizing processes are disqualified and new processes may be qualified in an effort to remove defect causing aspects associated with the cleaning and/or pellicle attachment procedures.

The system 10 thus provides an effective approach that may be employed to detect defects in a mask or reticle that increase as a function of increasing exposure, such as may occur during actual fabrication with the mask or reticle. While the exposure and post exposure inspect may add time to the reticle manufacturing process, it helps improve the reliability of the reticle and reticle manufacturing process by mitigating the occurrence of eventual defects. As a result, customer satisfaction improves.

Figure 2:
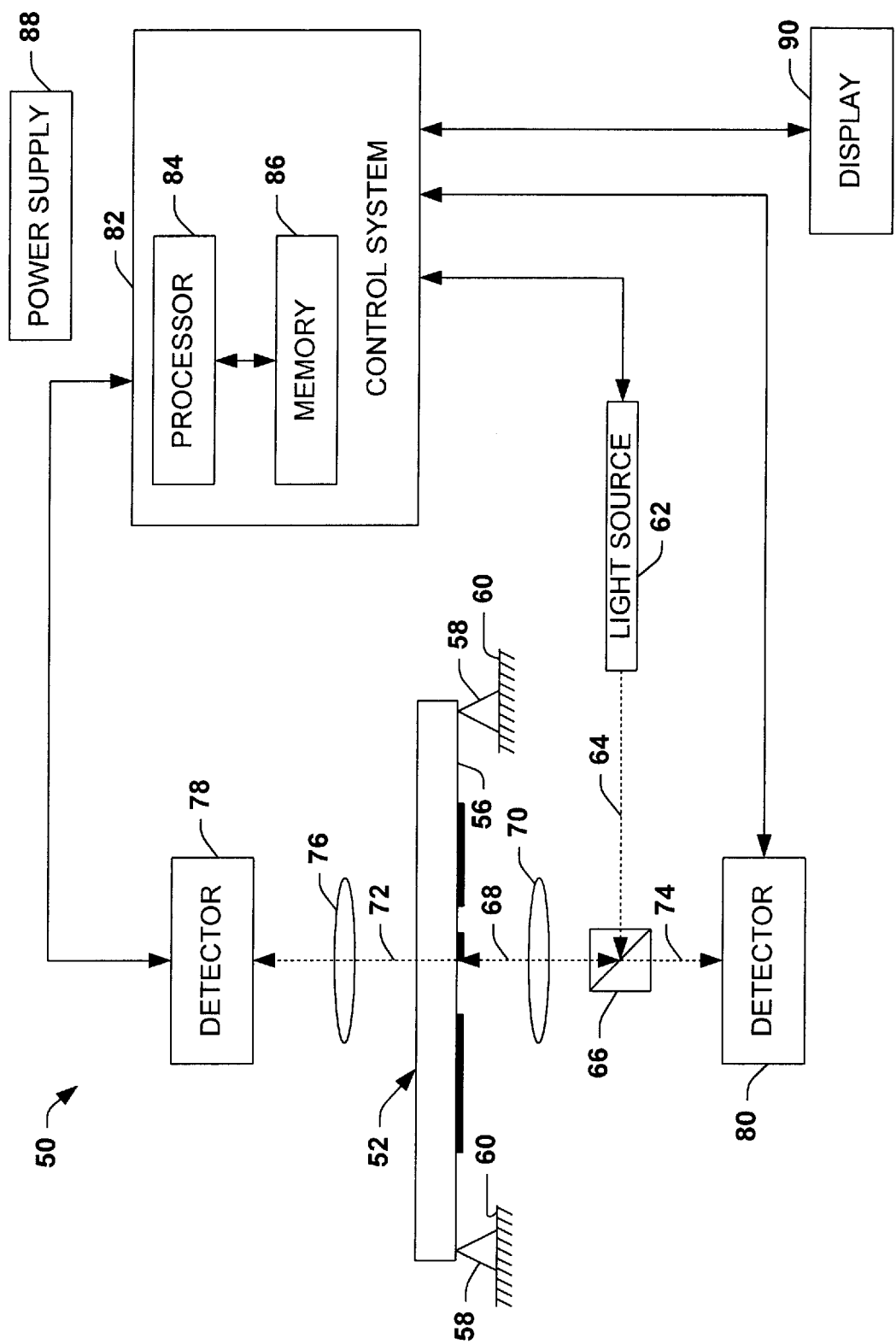
FIG. 2 is a functional block diagram of an example of a pre-pellicle inspection system in accordance with the present invention.

FIG. 2 illustrates a functional block diagram of an inspection system 50 that may employed to inspect a mask or reticle (hereinafter collectively referred to as "reticle") 52 for defects in accordance with an aspect of the present invention. In this example, the reticle 52 includes an image 54 at a bottom surface 56 of the reticle, such as formed in chromium. The reticle 52 is supported by supports 58 of a stage 60.

The system 50 includes a light source 62 to illuminate the reticle 52. The light source 62, which may include one or more lasers, provides incident light 64 to a reflector 66. The incident light 64 is reflected from the reflector 66 toward the reticle 52 as reflected light 68. The reflected light 68 passes through one or more lenses 70 to selectively illuminate part of the reticle.

Part of the reflected light 68 may be transmitted through the reticle 52 as transmitted light 72 and another part of the reflected light 68 may be reflected from the reticle as reflected light 74. The transmitted light 72 passes through one or more lenses 76 and is captured at a light detector 78. Similarly, the reflected light 74 is received at another light detector 80. Each of the light detectors 78, 80 are coupled to a controller 82 for providing signals that characterize the light captured by the respective light detectors. The light source 62 and the reflector 66 cooperate to illuminate each region of interest of the reticle 52, such as by rastering the reflected light 68 across the surface 58 of the reticle in a known manner.

The controller 82, for example, includes a processor 84, such as a microprocessor or CPU, coupled to a memory 86. The processor 84 receives measured data from the detectors 78 and 80. The controller 82 also is operatively coupled to the light source 62 to control the output of the incident beam 64. The controller 82 is programmed/and or configured to control and operate the various components within the inspection system 50 in order to carry out the various functions described herein.

The processor 84 may be any available processor. The manner in which the processor 84 can be programmed to carry out the functions relating to the present invention will be readily apparent to those having ordinary skill in the art based on the description provided herein.

The memory 86 serves to store program code executed by the processor 84 for carrying out operating functions of the system 50 as described herein. The memory 86 may include read only memory (ROM) and random access memory (RAM). The ROM contains among other code the Basic Input-Output System (BIOS) which controls the basic hardware operations of the system 50. The RAM is the main memory into which the operating system and application programs are loaded. The memory 86 also serves as a storage medium for temporarily storing information such as transmitted light data and reflected light data as well as algorithms that may be employed in carrying out the present invention. The memory 84 further may store data identifying characteristics for detected defects, such as may be derived from an analysis of the transmitted light data and reflected light data. For mass data storage, the memory 86 may include a hard disk drive.

Table I illustrates an example of the type of defect data that could be collected in accordance with an aspect of the present invention. By way of example, each defect identified from the detector signals may be provided a defect number (from 1 to N, where N is an integer identifying the number of defects). In addition, the defect data may include an indication of the position of the defect (e.g., in a coordinate system) relative to an identifiable location on the reticle 52, as well as an indication of the type, size, and severity of the detected defect. The defects may be classified into categories according to the type of defects, such as, for example, defects to the clear part of the reticle 52 (e.g., On Clear; Dim Clear), edge defects, unknown types of defects, a pin hole defects, a bright defects, defects on chrome features (e.g., On Chrome; Dim Chrome). The severity of the defect, for example, may indicate a PASS rating (when the defect is not severe), a FAIL rating (when the defect is extreme), or a WARNING rating (when it is not severe enough to merit a FAIL). The size of the defect may be selected from predetermine ranges of sizes or it may indicate a measurement of the size based on the detector data.

TABLE I

| DEFECT NO. | POSITION | TYPE | SIZE | SEVERITY |
| --- | --- | --- | --- | --- |
| 1 | X1, Y1 | T2 | B | PASS |
| 2 | X2, Y2 | T5 | A | FAIL |
| 3 | X3, Y3 | T2 | A | WARN |
| 4 | X4, Y4 | T1 | D | PASS |
| 5 | X5, Y5 | T1 | C | WARN |
| ... | ... | ... | ... | ... |
| N | XN, YN | T3 | E | PASS |

The system 50 also includes a power supply 88 that provides operating power to the system 50. Any suitable power supply (e.g., battery, line power) may be employed to carry out the present invention. The system 50 further may include a display 90 operatively coupled to the controller 82 for displaying a representation (e.g., graphical and/or text) of defect data collected for the reticle 52. The display 90 further may show a graphical and/or textual representation of the measured surface characteristics of the reticle 52.

While the example in the FIG. 2 illustrates simultaneous light transmitting and reflecting from a common light source 62 to inspect for defects, such as could include one of the STARlight inspection tools, it is to be appreciated that other inspection technologies also could be utilized in accordance with an aspect of the present invention. For example, a laser-scattering inspection technology and/or a light-based system having more than one light source also could be used in accordance with an aspect of the present invention.

Figure 3:
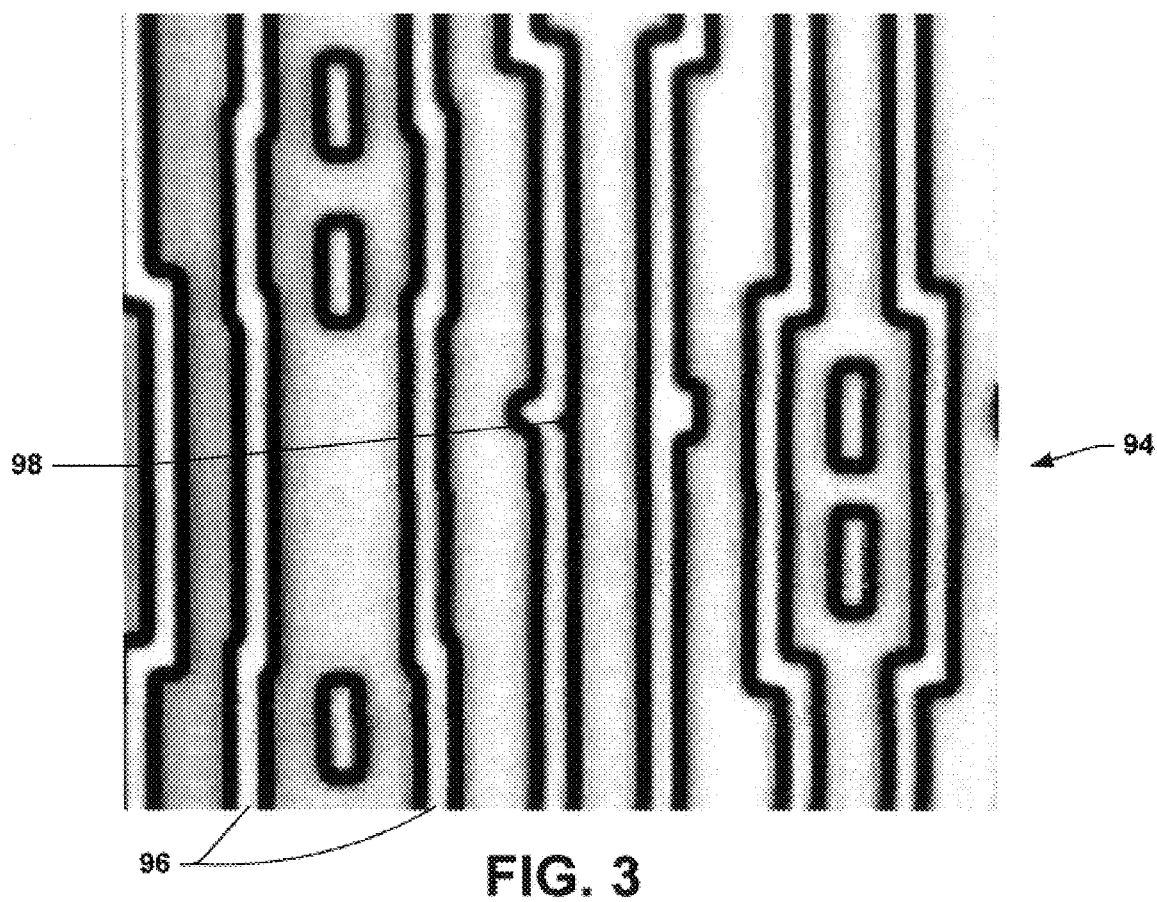
FIG. 3 is a representation of part of a reticle which may be detected with an inspection system in accordance with the present invention.

By way of illustration FIG. 3 illustrates an example of part of an image 94 generated by the inspection system 50 (FIG. 2) in accordance with an aspect of the present invention. The illustrated image 94 includes a representation of a pattern 96, such as formed of chromium on the reticle, which may be transferred to a wafer. In particular, a line of the pattern 96 includes a defect 98 near its edge. The defect 98, for example, corresponds to a contaminant that inhibits transmission and/or reflection of light through the reticle 52 being inspected by the system 50 (FIG. 2).

After a reticle passes an initial inspection, the mask or reticle may be exposed to a wavelength of light to implement an aging test in accordance with an aspect of the present invention. The aging test provides wavelength exposure to the reticle to simulate wavelength exposure that may occur during wafer fabrication. Because some defects may grow or change in response to exposure of the reticle, the aging test facilitates a determination as to whether the reticle includes defects that may develop or grow to become fatal defects. This type of defect could result in premature failure of a reticle due to wavelength exposure during fabrication. When such defects develop during fabrication, the reticle must be recleaned and re-pellicized if appropriate. Additional testing is performed to ensure that the resulting reticle is sufficiently free from defects so as to provide an adequate yield. Oftentimes, reticle manufacture does not occur at the same facility where the semiconductor fabrication is implemented, further increasing the down time. Therefore, one aspect of the present invention provides a system and method to mitigate the existence of defects that may vary as a function of exposure.

Figure 4:
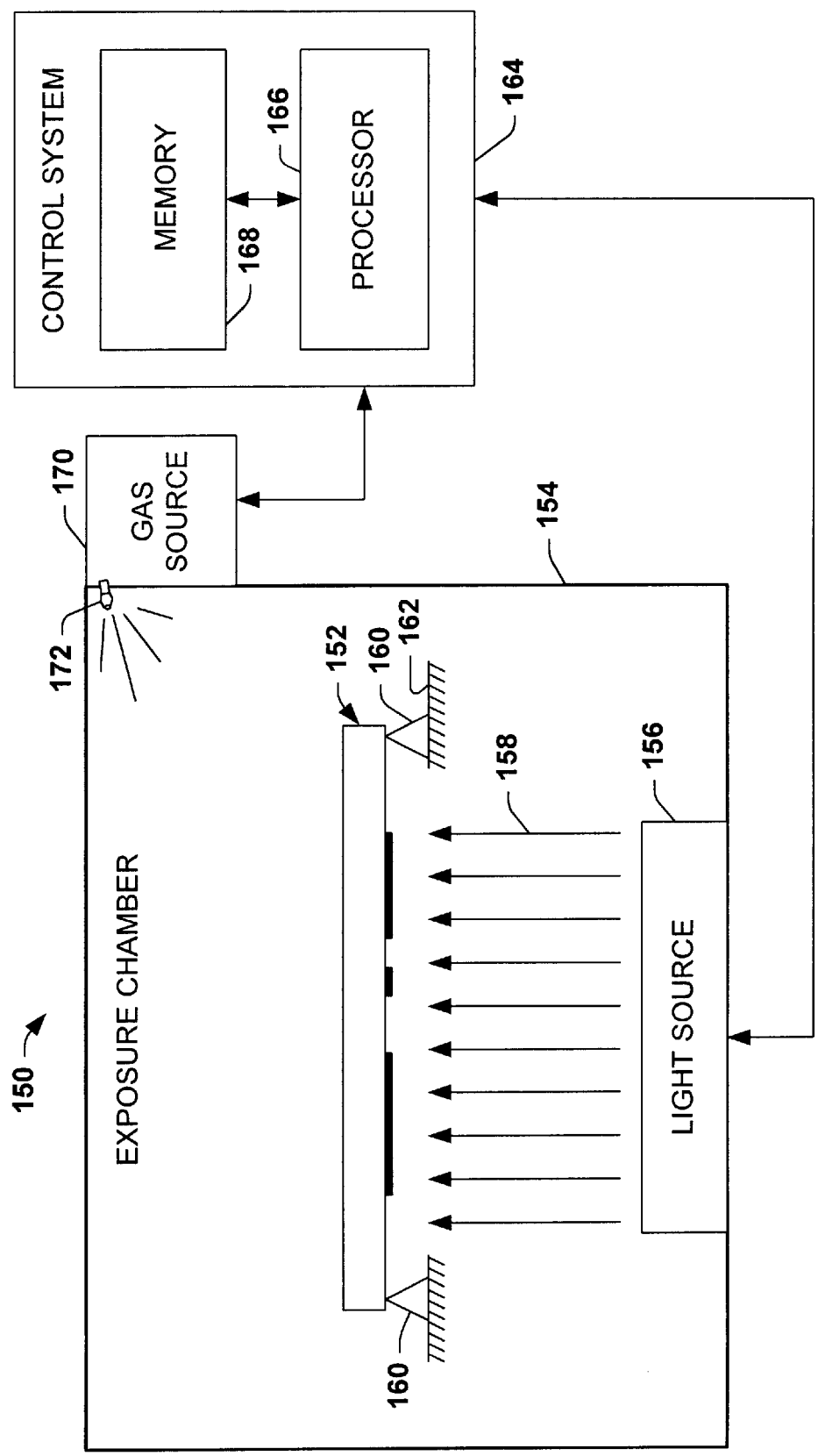
FIG. 4 is a functional block diagram of an example of an exposure system that may be utilized to expose a reticle or mask in accordance with the present invention.

In particular, FIG. 4 illustrates an example of an exposure system 150 that may be utilized to expose a mask or reticle (hereinafter referred collectively as "reticle") 152 to radiation in accordance with an aspect of the present invention. The exposure system 150, for example, is utilized after the inspection system 50 (FIG. 2) has completed inspection of the reticle 152 and the reticle passed the inspection. In the particular example in FIG. 4, no pellicle has been attached to the reticle 152.

The exposure system 150 includes an exposure chamber 154 having a light source 156 operative to expose the reticle 154 to a high or low energy wavelength exposure 158. In a particular aspect, the light source 156 provides short wavelength radiation 158, such as may have a specified wavelength less than about 300 nm. By way of example, the light source 154 may be operative to illuminate the reticle 152 light 158 having an exposure wavelength of 157 nm, 193 nm, or 248 nm. The chamber 154 also includes a support structure 160 associated with a stage 162 for supporting the reticle 152 in a position to receive the light 158.

A controller 164 is coupled to the light source 156 for controlling operation of exposure system 150. The controller 164, for example, includes a processor 166 coupled to memory 168 for controlling the system 150, such that the reticle 152 is illuminated for a desired time period. The processor 166 may receive feedback from the light source 156, such as a measure of the energy and/or wavelength of the light 156.

In accordance with an aspect of the present invention, the controller 164 controls the light source 156 to provide the light 158 to the reticle 152 for a time period and at an energy level that simulates actual exposure of the reticle during fabrication for a selected period of time. For example, the operating parameters may be set to simulate (in a shortened time period) the effects of fabrication over a period of one or more months, such as about three months. That is, assuming about ten hours of exposure daily for three months, the controller 164 may control the light source 156 to apply the light 158 for about 900 to about 1000 hours at the specified wavelength. In addition, the light 158 may be provided as numerous pulses during the exposure cycle (e.g., about 5000 to about 10000 pulses).

The manner in which the processor 166 can be programmed to carry out the functions relating to the present invention will be readily apparent to those having ordinary skill in the art based on the description provided herein. The memory 168 stores program code executed by the processor 166 for carrying out operating functions of the system 150 as described herein. For example, the memory 168 may store executable code that enables selection and control of the wavelength, energy, pulse rate, and the exposure cycle time period. After a desired amount of exposure, the reticle 152 may be removed from the exposure chamber 152 for performing a post-exposure inspection.

In accordance with an aspect of the present invention, the exposure system 150 may include a source 170 of an inert gas, such as Nitrogen ($N_2$) or Helium ($He_2$). A nozzle 172 is connected with the gas source 170 to enable flow of gas from the source into the exposure chamber 154. The controller 164 is coupled to the gas source 168 to selectively control the flow of gas into the exposure chamber 154. The controller 164 further may monitor and control the pressure within the chamber 154, temperature, gas concentration within the chamber, as well as moisture within the chamber. Thus, the exposure system 150 may control whether gas is applied into the chamber 154 during an exposure cycle.

By way of illustration, it may be desirable to apply the inert gas into the chamber for shorter wavelength radiation (e.g., 157 nm), as an ambient air environment, which may include $O_2$ and $H_2O$, tends to attenuate radiation at such short wavelengths. In addition, application of substantially dry $N_2$ gas into the chamber 154 simulates reticle exposure in a stepper and/or scanner environment in which ESD is more prevalent. Therefore, one can map defects for a reticle exposed in the chamber 154 both with and without $N_2$ so as to quantify the effects of ESD in a stepper/scanner environment.

In accordance with a particular aspect, no lens is interposed between the light source 156 and the reticle 152 in the exposure chamber 154, such that most of the exposure energy may be provided directly to the reticle. Because no lens is utilized, the lens material cannot absorb the energy, thereby facilitating transfer of energy from the light source 156 to the reticle 152. Thus, the arrangement in the exposure chamber 154 facilitates high energy transfer onto the reticle 152.

As just mentioned, post-exposure inspections may be implemented for wavelength exposure that occurs in an environment in which $N_2$ is supplied and in an environment without $N_2$ being applied. Referring back to FIG. 2, the reticle is inspected and data associated with the transmitted and reflected light is stored in associated memory 86. For example, the controller 82 constructs a graphical depiction of the features of the post-exposure reticle 52, including defects, similar to FIG. 3. The controller 82 further identifies defects on the reticle 126 and characterizes properties of the defects based on the transmitted and reflected light. Corresponding defect data may be analyzed and stored for each defect, such as described above with respect to Table I.

The graphical image of the post-exposure reticle further may be compared (e.g., by overlay) relative to a corresponding pre-exposure reticle to provide an indication of the differences between the conditions of the reticle. Additionally or alternatively, the defect data for each situation (pre- and post-exposure) may be correlated to provide an indication of the differences between such defect data. The differences, for example, indicate defects that may have been caused by the exposure. By way of illustration, the differences may identify defect formation and/or defect growth caused by radiation at exposure wavelengths. That is, the combination of pre- and post-exposure inspections enables an early determination of previously unnoticed fatal defects. As a result, contaminants and particulates left from, for example, a cleaning process may be quantified for defect growth or formation under wavelength exposure. The quantifiable results, in turn, may be employed to adjust manufacturing procedures to mitigate the occurrence of such defects.

By way of particular illustration, in a stepper environment, certain defects tend to cause an increase in electrostatic discharge (ESD) as a function of exposure during fabrication. By comparing the defect data for post-exposure inspection of a reticle that was exposed in an $N_2$ environment relative to defect data for a post-exposure inspection of a reticle that was exposed without $N_2$, one can quantify the effects of ESD in a stepper/scanner environment. The quantified results thus enable one to detect the build-up of ESD on the reticle. As a practical application, by implementing this type of inspection, in accordance with the present invention, a reticle manufacturer is provided the opportunity to reclean the reticle in an effort to remove such defects. By quantifying such data, one also may adjust the reticle manufacturing procedure to reduce the occurrence of such defects. As a result, the reliability of the reticle may be improved.

Another particular type of defect that may increase as a function of increasing exposure to DUV relates to changes in the chrome line on a reticle. By way of example, certain defects (e.g., edge defects) may increase in size due to increasing exposure to DUV. In particular, after repeated exposures, such defects may increase sufficiently in size to cause bridging between chrome lines. By detecting such defects prior to actual fabrication, the existence of such bridging between lines may be mitigated.

After a reticle passes both pre- and post-exposure inspection, for example, a pellicle 172 may be attached to a mask or reticle 174, such as illustrated in FIGS. 5 and 6. By way of example, the pellicle 172 includes a membrane 176, such as flouro polymer or other flexible light transmitting material (e.g., typically about a 99% transmission according manufacturing specifications). The membrane 176 is affixed to a frame 178, such as formed of aluminum, by a suitable adhesive material. The frame includes a venting hole 180 to permit the flow of ambient gases between the pellicle 172 and the reticle 174. The frame 178 is attached to the reticle 174 in overlying relation to the reticle pattern 182 by a suitable adhesive material to form a pellicized reticle 184, as shown in FIG. 6.

In the pellicized reticle 184, the membrane 176 is spaced apart from the image 182 formed on the reticle 174. As a result, particles and other contaminants residing on the pellicle membrane 176 are located at a sufficient distance from the reticle surface so as to have a negligible effect on the wafer image during exposure in wafer fabrication.

Figure 7:
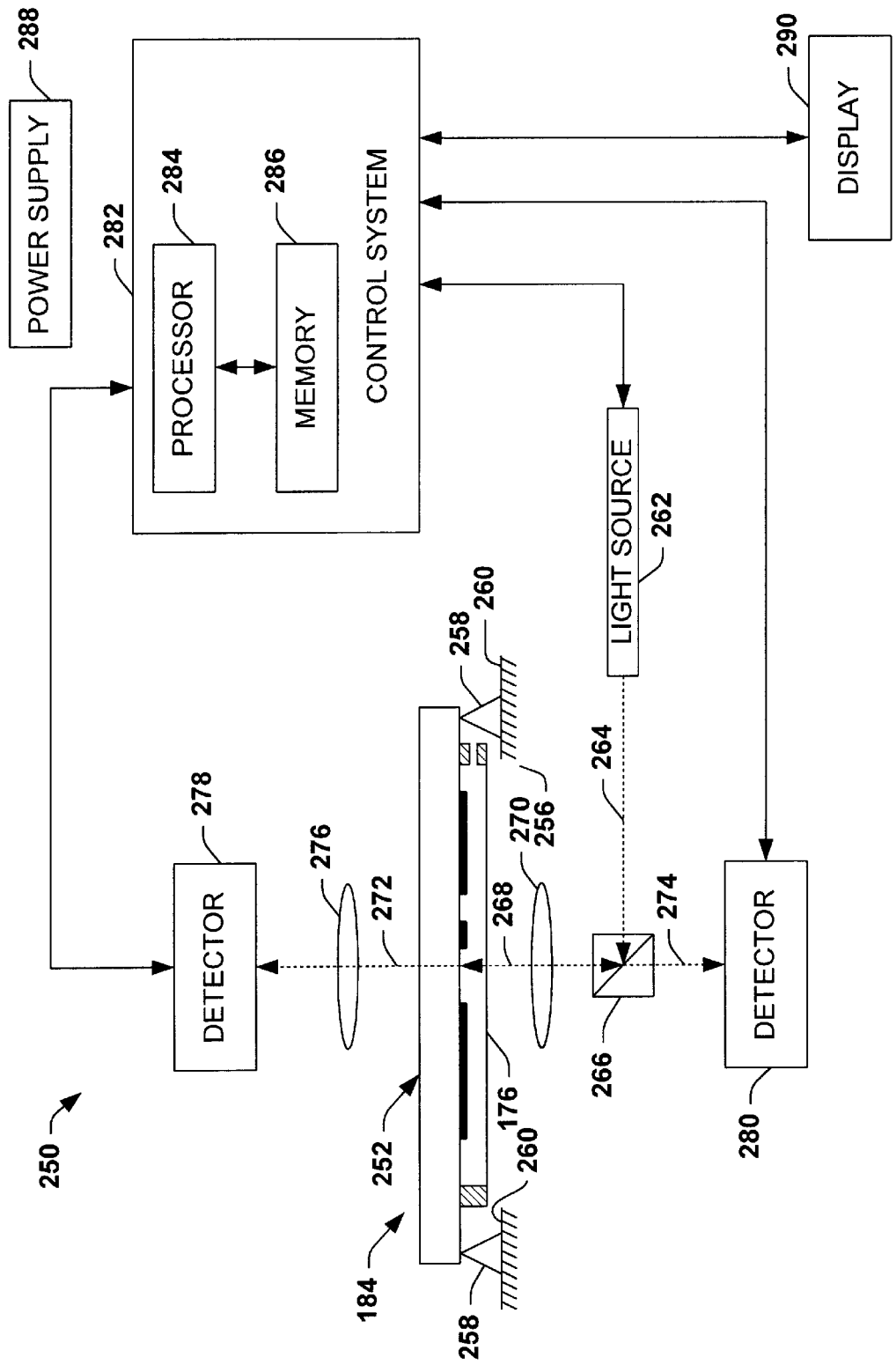
FIG. 7 is a functional block diagram of an example of a post-pellicle inspection system in accordance with the present invention.

After pellicle attachment, the pellicized reticle 184 is inspected for defects, such by an inspection system 250 illustrated in FIG. 7. For purposes of simplicity of explanation, it is assumed that the inspection systems of FIGS. 2 and 7 are substantially identical. Accordingly, the reference numbers in FIG. 7, which have been increased by adding 200 to the reference numbers of FIG. 2, correspond to parts previously identified with respect to FIG. 2.

Briefly stated, the system 250 includes a light source 262 that supplies light 264 applied to a reflector 266 that reflects light 268 onto the reticle assembly 184. The interaction of the light 268 results in transmitted and reflected light 272 and 274, respectively. The light 272 and 274 is received at respective light detectors 278 and 280, which provide corresponding signals to the controller 282. The controller 282 stores data associated with the transmitted and reflected light in associated memory 286. The controller 282 further is programmed and/or configured to construct a graphical depiction of the features of the reticle 184, such as similar to that illustrated in FIG. 3. The controller 282 further identifies defects on the pellicized reticle 184 and maps the defects based on the information from the detectors 278 and 280. The corresponding defect data may be analyzed and stored for each defect, such as in the manner described above with respect to Table I.

The controller 282 further may be programmed and/or configured to compare the defect data with the pre-pellicle defect data, such as to provide an indication of defects that may have been caused by attachment of the pellicle and/or cleaning. By way of illustration, the graphical depiction of the pre-pellicle reticle design may be overlayed relative to the image corresponding to the pellicized reticle to provide an indication of the differences between such images. The differences between the images (after appropriate adjustments due to sizing changes) provide an indication of new defects, such as may result from the pellicle attachment.

After the pellicized reticle 184 passes an inspection, such as with the system 250, the pellicized reticle may be exposed in an exposure system, which may be substantially similar to the system 150 shown and described with respect to FIG. 4.

Figure 8:
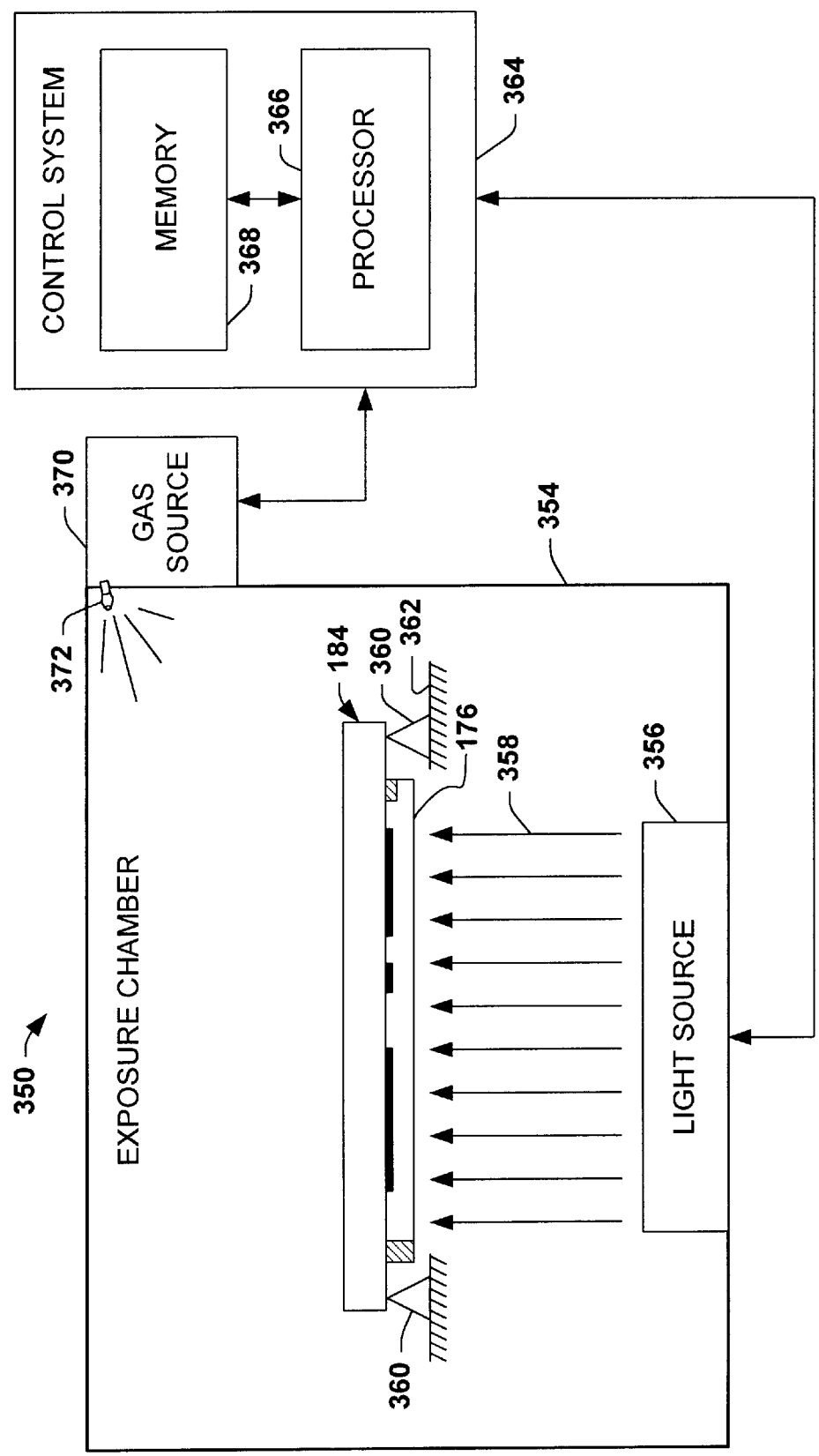
FIG. 8 is a functional block diagram of an example of an exposure system that may be utilized to expose a pellicized reticle or mask in accordance with the present invention.

FIG. 8 illustrates the pellicized reticle 184 being exposed in an exposure system 350, in which identical reference numbers, increased by adding 200, refer to corresponding parts previously identified with respect to FIG. 4. Because reference may be made to the description accompanying FIG. 4, a detailed description of FIG. 8 has been omitted for sake of brevity.

Briefly stated, the exposure system 350 includes an exposure chamber 354 having a light source 356 operative to provides short wavelength radiation 358, such as may have a specified exposure wavelength less than about 300 nm (e.g., 157 nm, 193 nm, 248 nm, etc.). A support structure 360 associated with a stage 362 supports the reticle 184 in a position to receive the light 358. A controller 364 is coupled to the light source 356 for controlling operation of exposure system 350. The controller 364, for example, includes a processor 366 coupled to memory 368. The memory stores computer-executable instructions for controlling flood exposure of the reticle 184 to the light 358 for a time period at a desired energy and wavelength. In accordance with an aspect of the present invention, the controller 364 controls the light source 356 to provide a specified wavelength of light 358 to the reticle 184 for a time period and at an energy level that simulates actual usage of the reticle during fabrication for a selected period of time. For example, the exposure system 350 may provide from about 5000 to about 10000 pulses of light at a specified wavelength, which pulses may vary depending on the energy level of the pulses.

In accordance with a particular aspect, the absence of a lens interposed between the light source 356 and the reticle 184 facilitates transfer of energy from the light source 356 to the reticle 184. Thus, the arrangement in the exposure chamber 354 provides for high energy transfer onto the reticle 184, such as may help reduce the overall exposure time in the system 350.

The exposure system 350 also may include a source of inert gas 370 in accordance with an aspect of the present invention. A nozzle 372 is in fluid communication between the gas source 370 and the interior of the exposure chamber 354, which is operative to provide gas into the chamber. By way of illustration, the gas source 368 may be operative to provide $N_2$ gas into the chamber so as to simulate a stepper/scanner environment in which ESD tends to occur, although any inert gas could be utilized. As a result, a $N_2$ rich environment enables one to measure the effects of ESD on the pellicized reticle 184 under exposure.

After the exposure cycle is completed, the reticle 126 is inspected to detect defects that may be attributed to the exposure process.

Referring back to FIG. 7, an example of an inspection that may be implemented to detect defects in a post exposure, pellicized reticle in accordance with an aspect of the present invention is illustrated. Briefly stated, the light source 262 provides light 264 that interacts with the reticle 184 to provide transmitted and reflected light 272 and 274, respectively. Light detectors 278 and 280 receive the light 272 and 274 and provide corresponding signals to the controller 282.

As mentioned above, the controller 282 stores data associated with the transmitted and reflected light in associated memory 286. For example, the controller 282 constructs a graphical depiction of the features of the post-exposure reticle 184, including defects, similar to FIG. 3. The controller 282 further may identify defects on the reticle 184 and characterize properties of the defects based on the transmitted and reflected light. Corresponding defect data may be analyzed and stored for each defect, such as in the manner described above with respect to Table I.

The controller 282 further may be programmed and/or configured to compare the post-exposure defect data with the pre-exposure defect data, such as to provide an indication of defects that may have been caused by exposure. Additionally or alternatively, post exposure defect data for reticle exposure with $N_2$ also may be correlated with post exposure defect data for reticle exposure without $N_2$, which may help quantify defects cause by ESD, such as may occur in a stepper/scanner system. As mentioned, the comparison, for example, may be made by graphical overlay and/or by correlating the defect data, which has been stored in connection with each inspection cycle.

Figure 9:
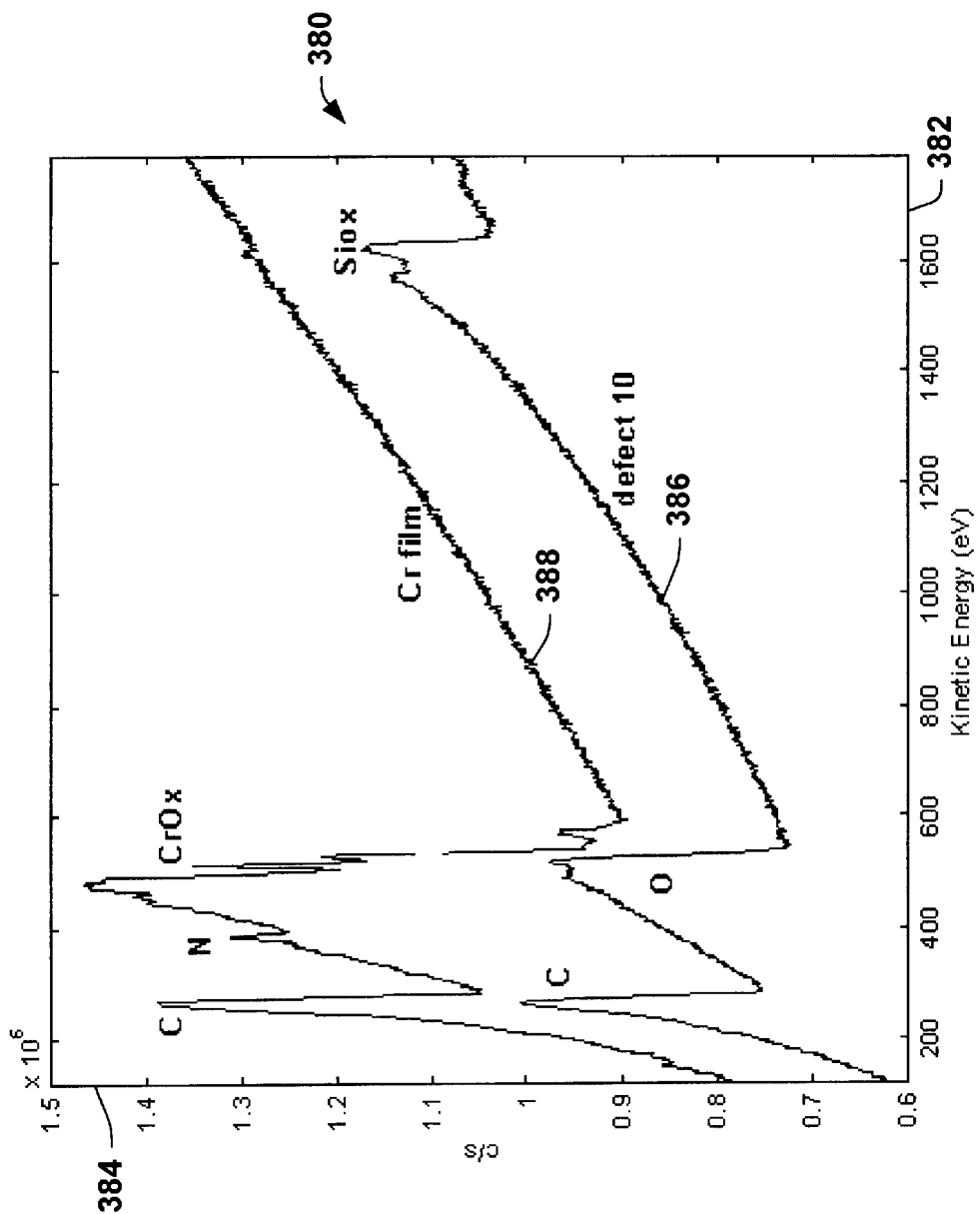
FIG. 9 is a graph illustrating chemical composition of parts of a post exposure mask or reticle in accordance with the present invention.

By way of illustration, if certain subpellicle defects exist, previously undetected defects may become visible to the inspection tool. By way of example, the fluoro polymers used in pellicles may chemically change under short wavelength (DUV) exposure, such as may result in an increase in defects containing fluorine and/or carbon. FIG. 9 illustrates a graph 380 in which kinetic energy (in electron volts) is represented on one axis 382 and a ratio of carbon to sulfur is represented on the other axis 384. The graph 380, for example, may be obtained by locating the defect with a scanning electron microscope and employing associated chemical analysis equipment to provide corresponding molecular compositions at selected locations of the reticle. The graph 380 includes a plot 386 of the molecular composition of a defect and another plot 388 of the composition of part of the reticle adjacent to the defect. In this particular example, the defect exhibits an increased carbon concentration. Because the pellicle is formed of fluoro polymers (e.g., $CF_2$), the increased carbon contamination may thus be caused by radiation of the pellicle membrane and/or pellicle adhesives at exposure wavelengths (e.g., DUV). It is to be appreciated that there may be similar increases in fluorine contaminants due to the exposure.

It also is to be appreciated that existing nonfatal defects could grow into fatal defects. That is, the correlation of pre- and post-exposure inspection data enables a determination of previously unnoticed fatal defects. As a result of employing an aging test for exposure-related defects, in accordance with an aspect of the present invention, the likelihood of premature reticle failure in the field may be mitigated.

By way of particular illustration, in a stepper environment, certain defects tend to cause an increase in electrostatic discharge (ESD) as a function of exposure during fabrication. By performing the post-exposure inspection of a pellicized reticle, in accordance with an aspect of the present invention, a build-up of ESD may be detected. This provides a reticle manufacturer the opportunity to reclean and re-pellicle a reticle in an effort to remove such defects and, in turn, improve the reticle reliability.

Another particular type of defect that may increase as a function of increasing exposure to DUV relates to changes in the chrome line on a reticle. By way of example, certain defects (e.g., edge defects) may increase in size due to increasing exposure to DUV, such as based DUV exposure reacting with the pellicle to increase fluorine and/or carbon concentrations. In particular, after repeated exposures, such defects may increase sufficiently in size to cause bridging between chrome lines.

It thus will be appreciated that a system or method according to the present invention provides an effective means to detect defects that may increase as a function of exposure so that appropriate steps may be taken to mitigate the occurrence of such defects. Accordingly, the present invention facilitates early detection of defects so as to increase the reliability of a reticle and mitigate undesirable down time.

Figure 10:
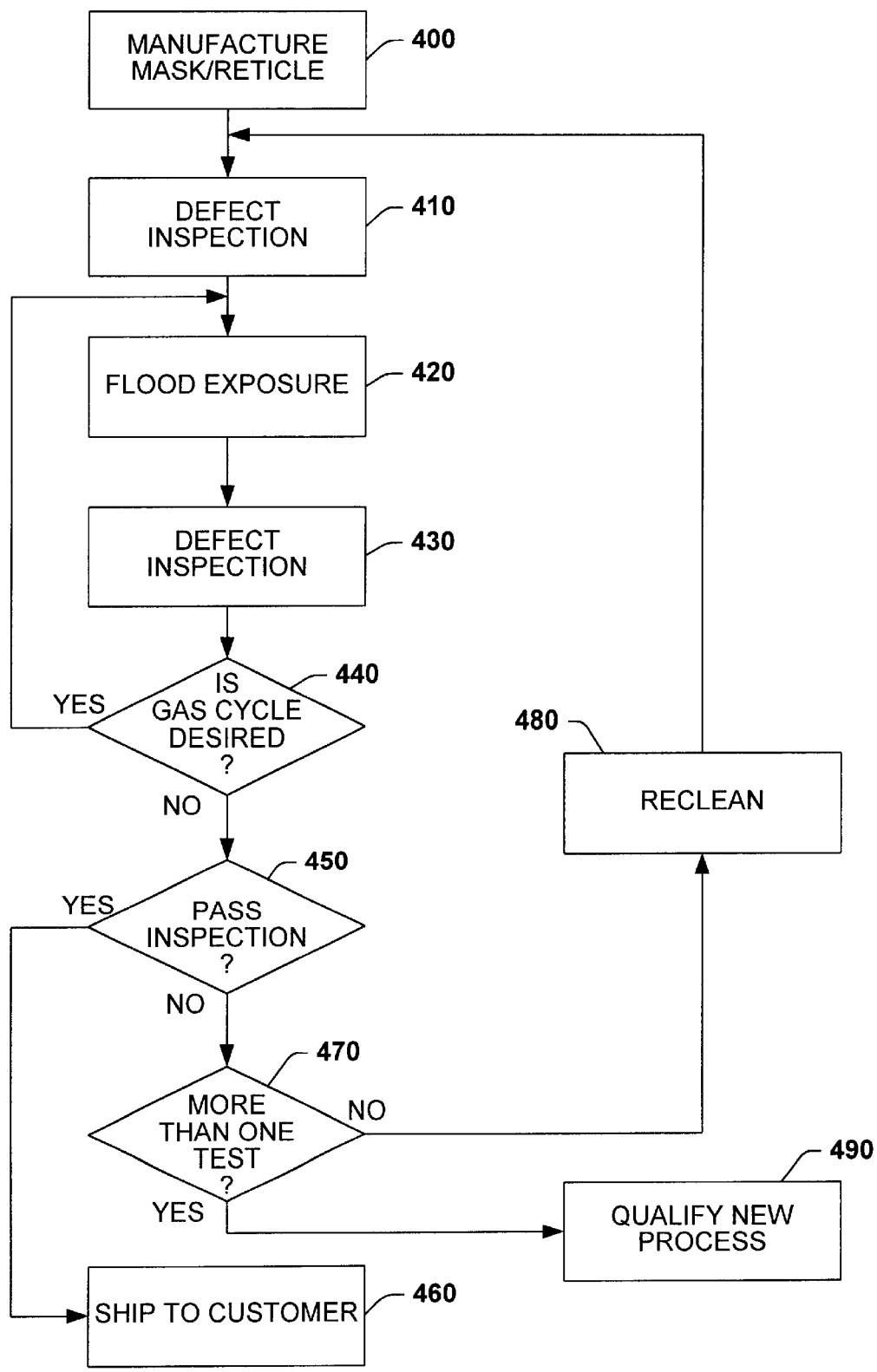
FIG. 10 is a flow diagram illustrating an example of a defect detection methodology in accordance with an aspect of the present invention.
Figure 11:
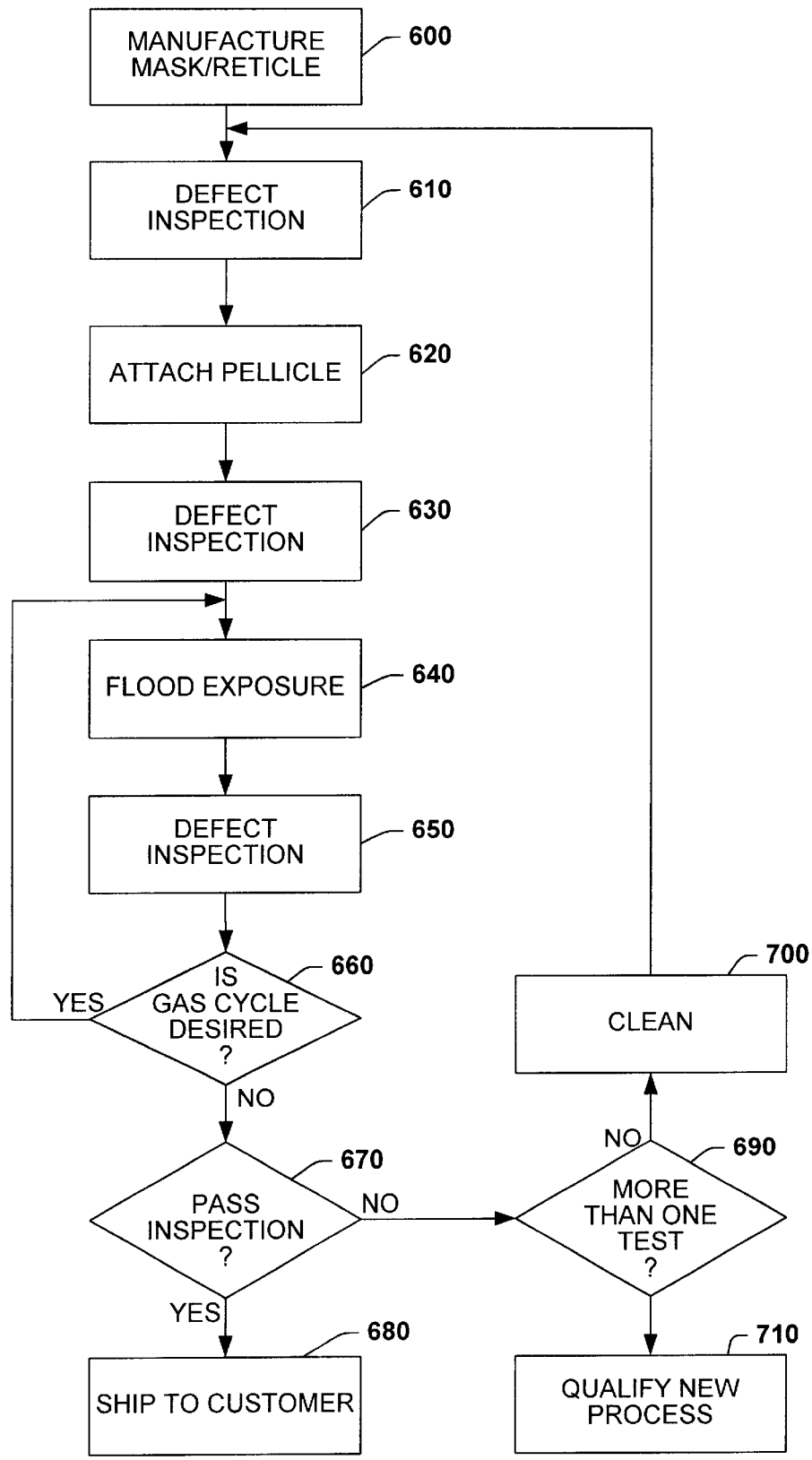
FIG. 11 is a flow diagram illustrating another example of a defect detection methodology in accordance with an aspect of the present invention

In view of the foregoing structural and functional features described above, methodologies that may be implemented in accordance with the present invention will be better appreciated with reference to FIGS. 10 and 11. While, for purposes of simplicity of explanation, the methodologies of FIGS. 10 and 11 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention. It is further to be appreciated that much of the following methodology may be implemented as computer-executable instructions, such as software stored in a computer-readable medium or as hardware or as a combination of hardware and software.

The methodology begins at 400 in which a pattern is formed on a blank mask or reticle. For example, the pattern formation may include generating a pattern and exposing the pattern on a chrome covered glass plate coated with photoresist. After an electron or laser beam has applied the pattern to the reticle, its surface is etched to remove the undesired portions of the chromium layer. The pattern area may be clear or opaque depending on the type of mask or reticle. After etching, the mask or reticle is cleaned so as to remove any remaining residue, resist, as well as particles. Those skilled in the art will understand and appreciate numerous procedures that could be employed to create a patterned reticle.

Next at 410, the reticle is inspected for defects. The defect inspection (410) may include a die-to-die inspection as well as a die-to-database inspection technology. The inspection further may include an inspection of all critical dimensions as well as an overlay test to ensure that the pattern has been appropriately formed on the reticle (or mask). Those skilled in the art will understand and appreciate that if certain types of defects are located during the inspection (410), such fatal defects may be repaired according to one or more known mask repair methodologies. Next, at 420, the reticle is illuminated, such as flood exposure to a short wavelength radiation. The exposure may be controlled to simulate exposure to a reticle during wafer fabrication. By way of particular illustration, the light may be DUV light having a predetermined wavelength less than about 300 nm (e.g., 157 nm, 193 nm, 248 nm, etc.). In accordance with a particular aspect, the exposure may continue for a time period that simulates an actual exposure cycle experienced by reticle during fabrication over a time period, such as up to about three months. The exposure may include numerous pulses (e.g., 5000 to about 10000) during an exposure cycle that may continue for about 75 to about 150 hours or as otherwise needed to implement a desired amount of wavelength exposure.

Next, at 430, a post-exposure defect inspection is performed. The post-exposure inspection collects data to characterize the features of the reticle including critical dimensions and defects. The collected data may be analyzed to characterize different attributes of the defects, such as may include an indication as to the type of defect, the position of the defect on the reticle, the severity of the defect, and the size of the defect. The data is stored and may be correlated with the inspection data collected at 410 to provide an indication of changes in the defects. The changes in the defects detected at 410 and 430 may be attributed to the exposure and used to provide an indication of possible early reticle failure.

Next at 440, a determination is made as to whether an exposure cycle in an inert gas environment, such as nitrogen or helium, and associated inspection is desired. If such a gas cycle is desired the process returns to 420 and the flood exposure is performed in the inert gas environment. For example, a desired concentration of the inert gas may be supplied into an exposure chamber prior to illumination of the reticle. The inert gas environment simulates exposure within a stepper and/or scanning tool in which ESD may build up and cause undesirable defects. The inert gas is particularly useful for shorter wavelength exposure, such as about 157 nm, as it facilitates transmission of the radiation energy in the exposure chamber. After radiation at an exposure wavelength in the inert gas environment, the reticle is inspected. After the inspection(s) have been completed, including for additional exposure in the inert gas environment, or if such additional exposure and inspection is not desired, the methodology proceeds to 450.

At 450, a determination is made as to whether the reticle passes the inspection(s) at 430. The determination may be based on a correlation between pre- and post-exposure inspection data. Additionally or alternatively, the determination may be based on a correlation of the inspection data for flood exposures that occurred in the inert gas environment and without additional inert gas. ESD, such as occurs in a stepper/scanner system, may cause extensive damage to a reticle. Therefore, by correlating defect data obtained for exposure implemented with nitrogen and without nitrogen, one may quantify the effects of ESD, such as occurs in a stepper/scanner environment.

If the reticle passes the inspection, the reticle is deemed appropriate for fabrication and may, in turn, be shipped to the appropriate customer at 460. If the determination at 450 is negative, indicating that the reticle has failed the post-exposure inspection (430), the methodology proceeds to 470. At step 470, a determination is made as to whether more than one aging test, in accordance with an aspect of the present invention, has been performed with respect to a given reticle. If the determination is negative, indicating a first aging test for the reticle, the methodology may proceed to 480.

At 480, the reticle is recleaned. From 480, the methodology returns to 410 in which the foregoing methodology is repeated.

If a given reticle fails the inspection a second time at 470, instead of proceeding to 480 to reclean and testing the reticle, the methodology proceeds to 490. At 490, the existing procedure is disqualified and a new process qualified in an effort to reduce defects associated with the manufacturing process, such as the cleaning. In particular, the defect data may be employed to quantify different aspects of the cleaning process, such that it may be adjusted to mitigate the occurrence of detected defects, including defects that increase as a function of short wavelength exposure.

FIG. 11 illustrates a methodology that may be implemented with respect to a mask or reticle to which a pellicle is attached. The methodology, for example, may be implemented subsequent to the defect detection methodology of FIG. 10. The methodology begins at 600 in which a patterned mask or reticle is manufactured.

Next at 610, the reticle is inspected for defects. The defect inspection at 610 may include a die-to-die inspection, die-to-database inspection, critical dimension inspection, and/or an overlay test to ensure that the pattern has been appropriately formed on the reticle (or mask). In addition, the defect inspection at 610 further may include a part of or the entire defect detection methodology shown and described with respect to FIG. 10. After the mask or reticle has been appropriately inspected for defects and passes the inspection, the methodology proceeds to 620.

At 620, a pellicle is attached to the mask or reticle. The pellicle includes a membrane that seals off the mask or reticle surface from airborne particulates as well as other forms of contamination. The membrane, which may be formed of a fluoro polymer material, is mounted on a rigid frame that is securely attached to the chromium side of the mask or reticle, such as shown and described with respect to FIGS. 5 and 6. Next, at 630, a post-pellicle defect inspection is performed. Such inspection, for example, may include a light transmitting, a light reflecting, and/or a laser scanning inspection technology.

From 630, assuming that the pellicized mask or reticle passes the inspection, the methodology proceeds to 640, in which the pellicized reticle is illuminated, such as by radiation with an exposure wavelength. By way of particular illustration, the light may include DUV radiation having a specified short wavelength (e.g., 157 nm, 193 nm, 248 nm, etc.). In accordance with a particular aspect, the exposure continues for a time period and under conditions that simulate actual exposure, which the reticle may experience during fabrication over a period of time, such as about zero to three months. That is, the exposure may provide about 5000 to about 10000 pulses of light at the specified wavelength, such as may correspond to about 800 to about 1000 hours of actual exposure. In order to facilitate such exposure, the radiation may be directly transmitted onto the mask or reticle (e.g., no intervening lenses between the source of illumination and the mask or reticle). As described with respect to FIG. 10, the exposure at 640 may be performed with and without nitrogen being supplied during the wavelength exposure cycle.

Next, at 650, a post-exposure defect inspection is performed. The post-exposure inspection collects data to characterize the features of the pellicized reticle, which may include critical dimensions and defects. The collected data may be analyzed to characterize attributes or properties of the defects, such as may include an indication as to the type of defect, the position of the defect on the reticle, the severity of the defect, and the size of the defect. From 650, the methodology proceeds to 660.

At 660, a determination is made as to whether an exposure cycle in an inert gas environment, such as nitrogen or helium, and associated inspection are desired. If such a gas test cycle is desired, the process returns to 640 and the flood exposure is performed in the inert gas environment. For example, a desired concentration of the inert gas may be supplied into an exposure chamber prior to illumination of the reticle. The inert gas environment simulates exposure within a stepper and/or scanning tool in which ESD may build up and cause undesirable defects. The inert gas is particularly useful for shorter wavelength exposure, such as about 157 nm, as it facilitates transmission of the short wavelength energy in the exposure chamber. After the additional radiation at an exposure wavelength in the inert gas environment, the reticle is inspected. After the inspection(s) have been completed, including for additional exposure in the inert gas environment, or if such additional exposure and inspection is not desired, the methodology proceeds to 670.

At 670, a determination is made as to whether the reticle passes the post-exposure inspection(s). This determination may be based on a comparison of the data collected in connection with the pre-exposure inspection at 610 and 630 as well as the post-exposure inspection at 650. By way of illustration, the post-exposure defect data may be compared with the pre-exposure defect data, such as to provide an indication of defects that may have been caused by the exposure at 640. Additionally or alternatively, post-exposure defect data for an exposure cycle with $N_2$ may be correlated with post-exposure defect data for a reticle exposure cycle without $N_2$. The correlation between post-exposure inspection data with and without $N_2$ helps quantify defects cause by ESD, such as is analogous to ESD defects that may occur in a stepper/scanner system. The comparison of inspection results, for example, may be made by graphical overlay and/or by correlating the defect data, which has been stored in connection with each inspection cycle.

If the reticle passes the post-exposure inspection (670), the methodology proceeds to 680 in which the reticle is deemed acceptable and may be shipped to the appropriate customer. If the determination at 670 is negative, indicating that the reticle has failed the post-exposure inspection (650), the methodology proceeds to 690 At step 690, a determination is made as to whether more than one aging test, in accordance with an aspect of the present invention, has been performed with respect to a given reticle under test. If the determination is negative, indicating a first aging test for the reticle, the methodology may proceed to 700. At 700, the reticle is recleaned and the methodology then returns to 610 in which the foregoing methodology is repeated.

If the determination at 690 indicates that a given reticle has failed the inspection a second time, the methodology proceeds to 710. At 710, existing procedures may be disqualified based on an analysis of the related inspection data. A new process may then be qualified in an effort to reduce defects associated with the manufacturing process, such as the cleaning, and the pellicle attachment. In particular, the defect data may be employed to quantify different aspects of the cleaning process. In addition the pre- and post pellicle data further enables the pellicle attachment procedure to be quantified. As a result, such procedures may be adjusted to mitigate the occurrence of detected defects, including defects that increase as a function of short wavelength exposure.

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for detecting defects in a patterned mask, comprising:
   an exposure system operative to illuminate the patterned mask for a time period; and
   an inspection system operative to collect data indicative of features and defects of the patterned mask, the inspection system being operative to detect changes in the features and defects of the patterned mask caused by the illumination of the patterned mask indicative of defects in the patterned mask.

2. The system of claim 1, wherein the exposure system further comprises an exposure chamber that includes a light source operable to illuminate the patterned mask with short wavelength radiation.

3. The system of claim 2, wherein the light source is operable to apply light having a deep ultra violet wavelength.

4. The system of claim 3, wherein the light source is operable to apply light having a wavelength less than about 300 nanometers.

5. The system of claim 4, wherein the light source is operable to apply light having a wavelength selected from at least one of 157 nanometers, 193 nanometers, and 248 nanometers.

6. The system of claim 2, further comprising a controller coupled to the light source and operative to control light from the light source.

7. The system of claim 6, wherein the controller is programmed to control the light source to apply light that simulates exposure associated with semiconductor fabrication over a simulated time period less than about six months.

8. The system of claim 7, wherein the simulated time period ranges from about one month to about three months.

9. The system of claim 6, further comprising a gas source operably associated with the exposure chamber to supply an inert gas into the exposure chamber, the controller being operative to control flow of the inert gas from the gas source into the exposure chamber.

10. The system of claim 9, wherein an interior of the exposure chamber provides an exposure environment, the controller being operative to control the exposure environment to facilitate transmission of the illumination onto the mask.

11. The system of claim 2, further comprising a gas source operably associated with the exposure chamber to supply an inert gas into the exposure chamber.

12. The system of claim 11, wherein the inert gas further comprises nitrogen.

13. The system of claim 11, further comprising a controller coupled to the gas source and operative to control the flow of the inert gas from the gas source into the exposure chamber.

14. The system of claim 1, wherein the inspection system further comprises a source of light that applies incident light to the mask and a detector operative to detect at least one of transmitted and reflected light from the mask and provide the data indicative of the features and defects of the mask based on the at least one of transmitted and reflected light.

15. The system of claim 1, wherein the inspection system further comprises a control system having memory operative to store the collected data indicative of the features and defects of the mask.

16. The system of claim 15, wherein the control system further comprises computer-executable instructions to correlate pre-exposure and post-exposure defect data for the mask and provide an indication of defects that vary as a function of exposure based on the correlation.

17. The system of claim 16, wherein the control system is operative to compare the pre-exposure and post-exposure defect data to identify defects in the patterned mask caused by illumination of the exposure system.

18. The system of claim 17, wherein the control system is operative to compare the pre-exposure and post-exposure defect data to identify increases in number of defects caused by illumination of the exposure system.

19. The system of claim 17, wherein the control system is operative to compare the pre-exposure and post-exposure defect data to identify defects that increase in size caused by illumination of the exposure system.

20. The system of claim 17, wherein the control system is operative to compare the pre-exposure and post-exposure defect data to quantify effects of electrostatic discharge based on the comparison of defect data.

21. The system of claim 15, further comprising a pellicle attached to the mask, wherein the defects in the mask caused by the light applied by the exposure system correspond to subpellicle defects.

22. The system of claim 1, further comprising a pellicle attached to the mask to define a pellicized mask, wherein the inspection system is operative to detect defects in the pellicized mask caused by illumination of the exposure system.

23. The system of claim 22, wherein the detected defects further comprise a degradation in transmission through the pellicle due to illumination of the pellicized mask in the exposure system.

24. A system for detecting defects in a patterned mask, comprising:
    means for illuminating the patterned mask with an exposure wavelength; and
    means for inspecting the patterned mask and collecting data indicative of features and defects of the patterned mask; and
    means for correlating the collected data to identify defects in the patterned mask cause by illumination of the patterned mask.

25. The system of claim 24, wherein the exposure wavelength further comprises a deep ultra violet wavelength.

26. The system of claim 24, wherein the exposure wavelength further comprises less than about 300 nanometers.

27. The system of claim 24, wherein the illuminating means further comprises an enclosure, the system further comprising means for providing an inert gas into the enclosure.

28. The system of claim 27, further comprising control means for controlling operative to control an environment within the enclosure to facilitate illumination of the mask.

29. The system of claim 24, further comprising means for correlating pre-exposure and post-exposure defect data for the mask and identifying defects that vary as a function of exposure based on the correlation.

30. The system of claim 24, further comprising means for attaching a pellicle to the mask, the means for illuminating and the means for inspecting being operable to respectively inspect, illuminate and inspect the mask before and after the pellicle is attached, wherein a correlation of inspection data before illumination and inspection data after illumination of the pellicized mask identifies subpellicle defects caused by illumination.

31. A method for detecting defects in a mask, comprising:
    inspecting the mask and generating pre-exposure inspection data;
    exposing the mask to short wavelength radiation;
    inspecting the exposed mask and generating post-exposure inspection data; and
    determining defects in the mask functionally related to the exposure based on the pre-exposure and post-exposure inspection data.

32. The method of claim 31, further comprising providing an inert gas into an environment in which the exposure occurs, the post-exposure inspection data including an indi cation of effects of the inert gas on the mask during the exposure.

33. The method of claim 32, further comprising controlling the environment in which the exposure occurs to facilitate illumination of the mask.

34. The method of claim 31, wherein the exposure wavelength further comprises a deep ultra violet wavelength.

35. The method of claim 34, wherein the exposure wavelength further comprises less than about 300 nanometers.

36. The method of claim 31, further comprising:

attaching a pellicle to the mask to define a pellicized mask;

inspecting the pellicized mask and generating pre-exposure, pellicle inspection data;

exposing the pellicized mask to short wavelength radiation;

inspecting the exposed pellicized mask and generating post-exposure, pellicle inspection data; and determining defects in the mask functionally related to the exposure and attachment of the pellicle based on the pre-exposure and post-exposure pellicle inspection data.

* * * * *